(12) United States Patent
Lin et al.

(10) Patent No.: US 10,160,782 B2
(45) Date of Patent: Dec. 25, 2018

(54) METHODS FOR PREPARING DEOXYCHOLIC ACID

(71) Applicant: NORATECH PHARMACEUTICALS, INC., Taipei (TW)

(72) Inventors: Cheng-Gang Lin, Nanjing (CN); Li Gui, Nanjing (CN); Pan Chen, Nanjing (CN); Zhi-Xuan Wang, Nanjing (CN); Tong-Wei Guan, Nanjing (CN); Yuan-Yuan Yin, Nanjing (CN); Yu-Ling Lu, Nanjing (CN)

(73) Assignee: NORATECH PHARMACEUTICALS, INC., Taipei (TW)

( * ) Notice: Subject to any disclaimer, the term of this patent is extended or adjusted under 35 U.S.C. 154(b) by 0 days.

(21) Appl. No.: 15/566,097

(22) PCT Filed: Feb. 26, 2016

(86) PCT No.: PCT/CN2016/074662
§ 371 (c)(1),
(2) Date: Oct. 12, 2017

(87) PCT Pub. No.: WO2016/165496
PCT Pub. Date: Oct. 20, 2016

(65) Prior Publication Data
US 2018/0111960 A1    Apr. 26, 2018

(30) Foreign Application Priority Data

Apr. 14, 2015 (CN) .......................... 2015 1 0174017

(51) Int. Cl.
| | | |
|---|---|---|
| *C07J 9/00* | (2006.01) |
| *C07D 317/72* | (2006.01) |
| *C07J 1/00* | (2006.01) |
| *C07J 13/00* | (2006.01) |
| *C07J 21/00* | (2006.01) |

(52) U.S. Cl.
CPC ............. *C07J 9/005* (2013.01); *C07J 1/0011* (2013.01); *C07J 13/007* (2013.01); *C07J 21/008* (2013.01)

(58) Field of Classification Search
CPC ............................... C07J 9/005; C07D 317/72
USPC .......................................... 552/549; 549/336
See application file for complete search history.

(56) References Cited

U.S. PATENT DOCUMENTS 7,994,351 B2 *    8/2011    Prasad ....................... C07J 1/00
552/549

* cited by examiner

*Primary Examiner* — Charanjit Aulakh
(74) *Attorney, Agent, or Firm* — Birch, Stewart, Kolasch & Birch, LLP

(57) ABSTRACT

The present invention discloses method for preparing deoxycholic acid (DCA) or an ester thereof or a pharmaceutically acceptable salt thereof. Said compounds may be applied to remove a fat deposition.

7 Claims, No Drawings

METHODS FOR PREPARING DEOXYCHOLIC ACID

FIELD OF THE INVENTION

The present invention relates to the field of pharmaceutical organic synthesis, and in particular, to a novel method for preparing deoxycholic acid or an ester thereof, or a pharmaceutically acceptable salt thereof, and an intermediate thereof.

BACKGROUND OF THE INVENTION

Quick removal of fat is an ancient ideal. Papers reported that deoxycholic acid has fat removal properties when injected to a fat deposition site in the body. At present, deoxycholic acid is mainly derived from an animal body. Although the cost is relatively low, but there exists a risk that it may contain animal pathogens and other harmful factors.

In order to realize the full potential of deoxycholic acid in removing fat and to solve the problems brought about by animal-derived products, the present invention provides a method for chemically synthesizing a deoxycholic acid. The resultant products not only have high yield, high purity, but also are applicable by quality control and convenient for industrial production.

BRIEF SUMMARY OF THE INVENTION

The present invention provides a method for preparing deoxycholic acid (DCA) or an ester thereof or a pharmaceutically acceptable salt thereof:

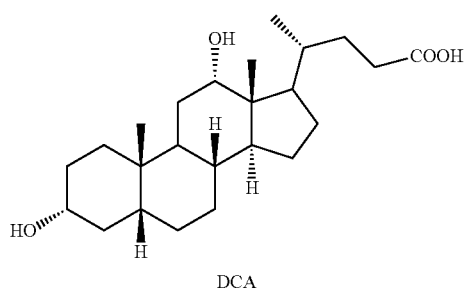

DCA said method comprising, g) reacting the compound of formula 1 with methyl acrylate in the presence of a Lewis acid to form a compound of formula 2

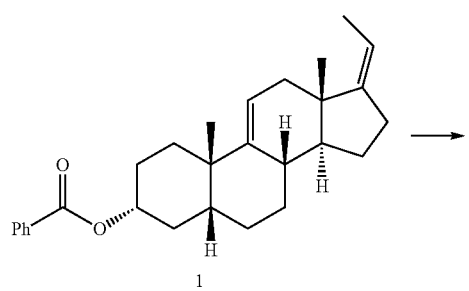

1

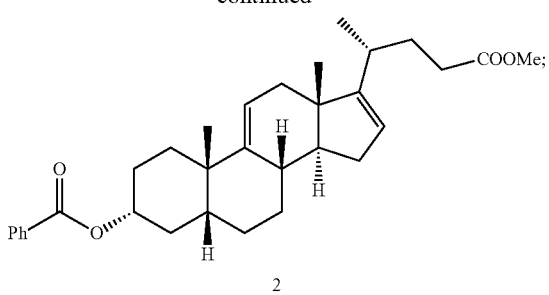

2 h) reacting the compound of formula 2 with $H_2$ under a hydrogenation condition to form a compound of formula 3

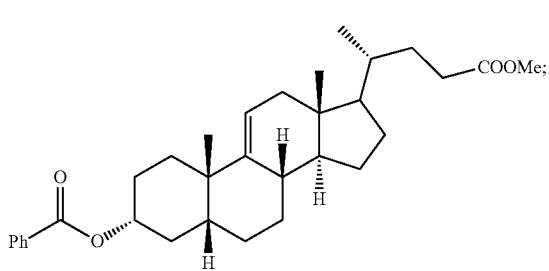

3 i) reacting the compound of formula 3 with an oxidizing agent to form a compound of formula 4

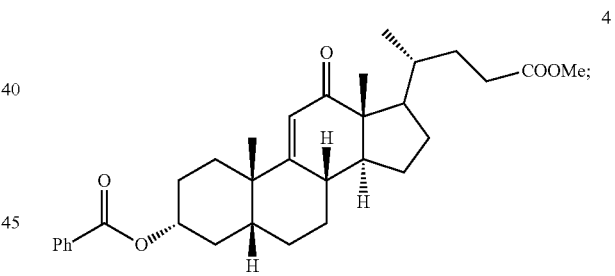

4 j) reacting the compound of formula 4 with $H_2$ under a hydrogenation condition to form a compound of formula 5

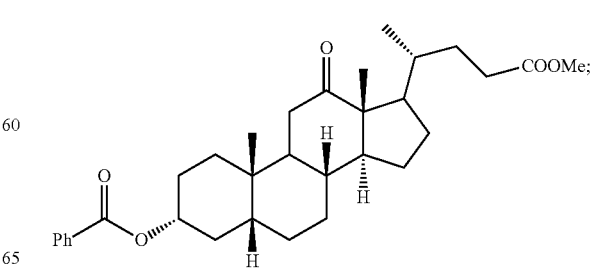

5 k) reacting the compound of formula 5 with a reducing agent to form a compound of formula 6

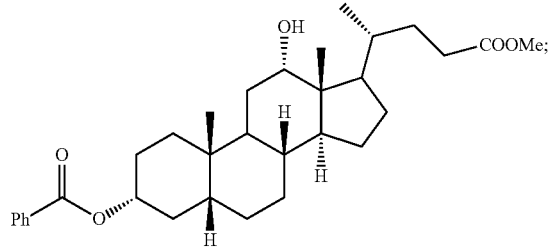

and l) exposing the compound of formula 6 to a deprotection condition to form an ester thereof, and optionally, exposing to a suitable hydrolysis condition to form a deoxycholic acid or a pharmaceutically acceptable salt thereof.

In one embodiment, the Lewis acid in g) is EtAlCl$_2$.

In one embodiment, the hydrogenation condition in h) comprises pd/C or PtO$_2$ as a catalyst.

In one embodiment, the hydrogenation condition in i) comprises tert-butylhydroperoxide and pyridinium chlorochromate.

In one embodiment, the hydrogenation condition in j) comprises pd/C or PtO$_2$ as a catalyst.

In one embodiment, the reducing agent in k) is LiAl(OtBu)$_3$H.

In one embodiment, the deprotection and hydrolysis conditions in l) comprise reacting the compound of formula 6 with an alkali metal hydroxide, an alkali metal alcoholate, an alkaline earth metal hydroxide, an alkaline earth metal alcoholate, or a mixture thereof. In some aspects, the hydrolysis condition comprises an acid treatment to obtain the deoxycholic acid. In other aspects, the acid treatment is omitted to obtain corresponding salts.

In one embodiment, the alkali metal hydroxide is NaOH.

In one embodiment, a salt of deoxycholic acid may be prepared by reacting with an alkaline earth metal alcoholate or hydroxide. Salts of deoxycholic acid include sodium, potassium or lithium salts.

In one embodiment, provided is an intermediate compound selected from the group consisting of:

(Z)-3α-benzoxy-5β-pregna-9 (11), 17 (20)-diene (1);
(E)-3α-benzoxy-5β-cholo-9 (11), 16-diene-24-acid methyl ester(2);
3α-benzoxy-5β-cholo-9(11)-alkene-24-acid methyl ester (3);
3α-benzoxy-5β-cholo-9(11)-en-12-ketone-24-carboxylate (4);
3α-benzoxy-5β-cholane-12-ketone-24-acid methyl ester(5);
3α-benzoxy-5β-cholo-9(11)-en-12-hydroxy-24-acid methyl ester(5a);
3α-benzoxy-5β-cholane-12β-hydroxy-24-acid methyl ester (5b); and
3α-benzoxy-5β-cholane-12α-hydroxy-24-acid methyl ester (6).

In one preferred embodiment, deoxycholic acid or an ester thereof or pharmaceutically acceptable salt thereof of the present invention is prepared by the following method:

The method comprising:

g) reacting the compound of formula 1 with methyl acrylate in the presence of a Lewis acid to form a compound of formula 2 h) reacting the compound of formula 2 with H$_2$ under a hydrogenation condition to form a compound of formula 3 i) reacting the compound of formula 3 with an oxidizing agent to form a compound of formula 4 (The compound of formula 3 (1.2%)<2% is monitored by HPLC (area normalization method), stopping the reaction, quenching, and treating the reaction; followed by the addition of pyridinium chlorochromate, and a compound of formula 4a is formed in the oxidation reaction to obtain the compound of formula 4)

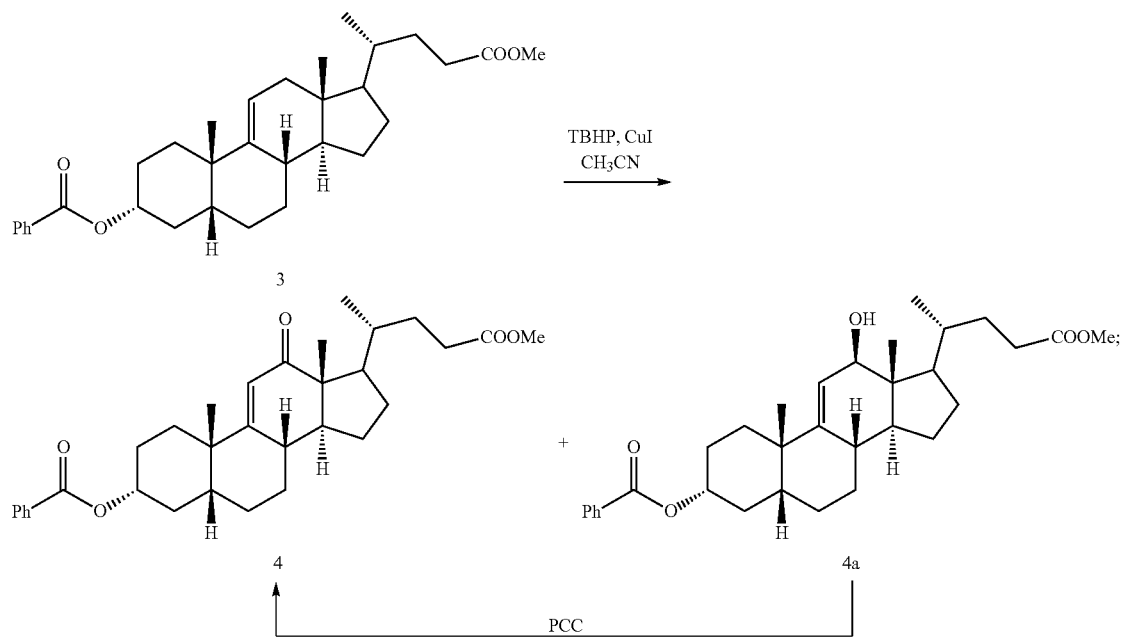

j) reacting the compound of formula 4 with $H_2$ under a hydrogenation condition to form a compound of formula 5 (stopping the reaction and adding pyridinium chlorochromate to oxidize compound 5a and compound 5b formed in the reaction process, respectively, and compound 4 obtained thereby continuing to react with $H_2$ under hydrogenation condition to obtain compound 5; cycling the operation as such to increase the yield of compound 5

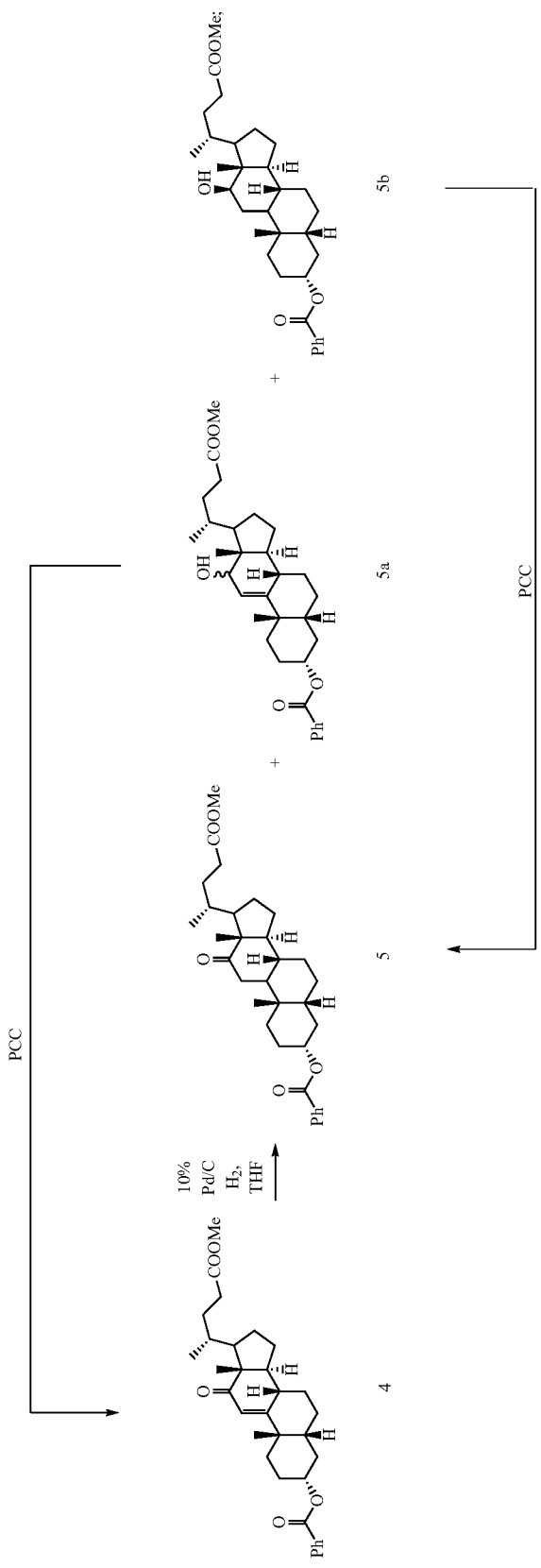

k) reacting the compound of formula 5 with a reducing agent to form a compound of formula 6

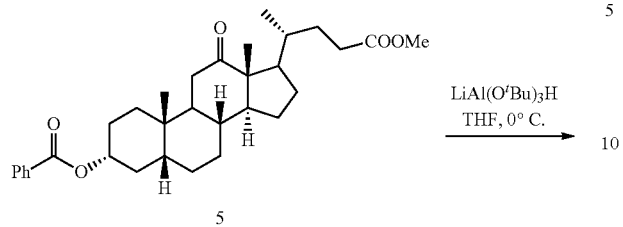

5

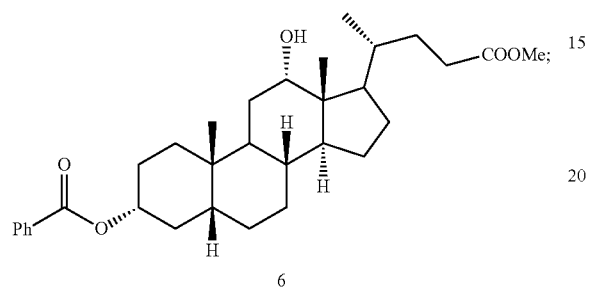

6 and l) exposing the compound of formula 6 to a deprotection condition to form an ester thereof, and optionally, exposing to a suitable hydrolysis condition to form a deoxycholic acid or a pharmaceutically acceptable salt thereof. Said suitable hydrolysis condition is an NaOH solution.

In one embodiment, compound 1 of the present invention is prepared by the following method:

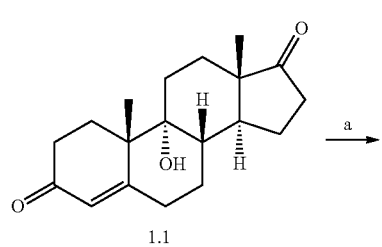

1.1

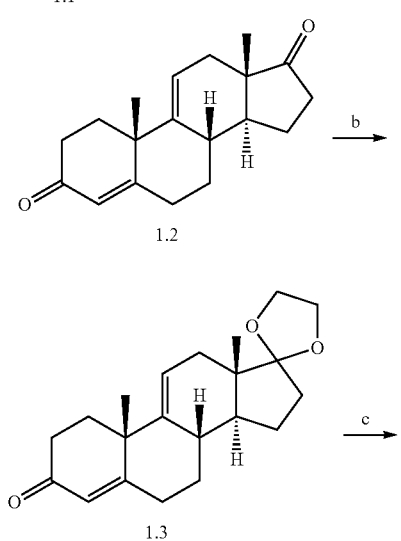

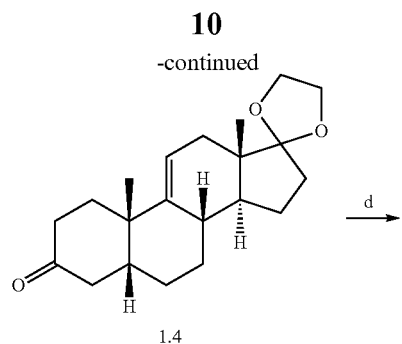

1.4

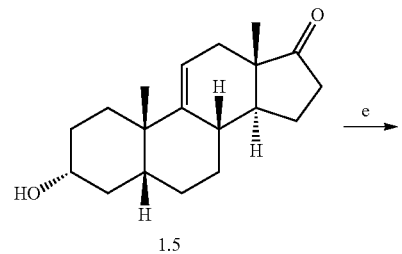

1.5

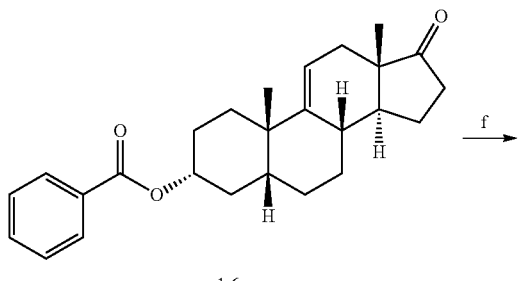

1.6

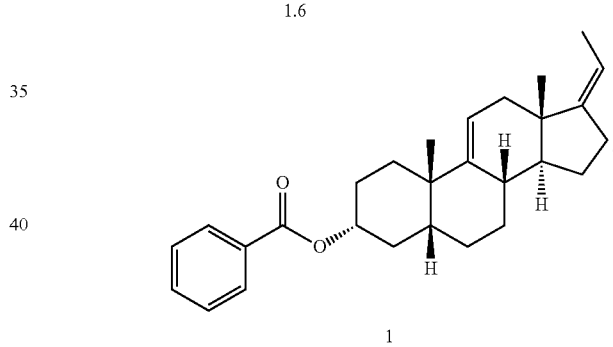

1 a) CH$_2$Cl$_2$, H$_2$SO$_4$; b) TsOH, toluene; c) 10% Pd/C, NMP, H$_2$; d) 1. LiAl($^t$BuO)$_3$, THF 2. TsOH; e) Benzoyl Chloride, DMAP, TEA; f) Ph$_3$PCH$_2$CH$_3$Br, KO$^t$Bu, THF In one embodiment, compound 1.4 of the present invention is prepared by the following method:
Reacting the compound of formula 1.3 with H$_2$ at room temperature to form the compound of formula 1.4, with N-Methylpyrrolidone as a solvent and 10% pd/C as a catalyst

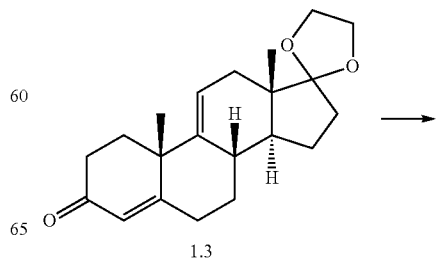

1.3

-continued

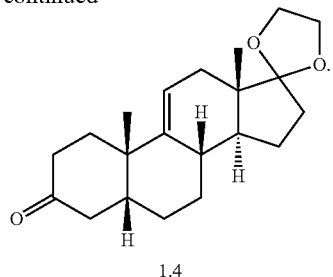

1.4

As used herein, the term "Lewis acid" refers to an electron pair acceptor, which includes but is not limited to $EtAlCl_2$, aluminum chloride, ferric chloride, boron trifluoride, niobium pentachloride and triflate of lanthanide.

The term "hydrogenation agent" refers to a reagent able to provide hydrogen to a molecule.

DETAILED DESCRIPTION OF THE INVENTION

The present invention is illustrated below by non-limiting examples. It is to be understood that the preferred embodiments described herein are provided for the purpose of demonstration rather than limitation.

Example 1: Synthesis of Compound 1.2

Dichloromethane (2.0 L, 8 V) and compound 1.1 (250.0 g, 826.5 mmol) were added to a 5 L three-necked flask, and stirred and heated until dissolved. Concentrated sulfuric acid (124.0 g, 1240.0 mmol, 98%) was dropwise added to the reaction solution. The reaction solution was heated to reflux, stirred for 4 h, and the reaction was stopped.

After the reaction solution was cooled, it was slowly poured into 1 L of iced water and stirred for 5 min, followed by the dropwise addition of saturated sodium carbonate solution to adjust pH to 7 to 8. The mixture was transferred to a separatory funnel and was extracted twice with $CH_2Cl_2$ (200 mL, 0.8 V), and the organic phase was combined. The organic phase was washed with water (500 mL, 2 V) and saturated brine (500 mL, 2 V) and dried over anhydrous sodium sulfate. After drying, the organic phase was obtained by filtration. The organic phase was removed by rotary evaporation to obtain a crude product. At room temperature, the crude product was beating washed with Ethyl acetate (375 mL, 1.5 V) for 12 h and filtered. The filter cake was washed with ethyl acetate (50 mL, 0.2 V), drained, and vacuum dried under 20-40° C. to obtain compound 1.2 (211.0 g, yield: 89.7%).

$^1$H-NMR (400 MHz, $CDCl_3$) δ:5.76 (s, 1H), 5.64-5.45 (m, 1H), 2.70-2.33 (m, 6H), 2.23-2.02 (m, 7H), 1.72-1.56 (m, 1H), 1.57-1.45 (m, 1H), 1.36 (s, 3H), 1.27-1.08 (m, 1H), 0.89 (s, 3H).

Example 2: Synthesis of Compound 1.3

Compound 1.2 (200.0 g, 703.3 mmol), ethylene glycol (261.9 g, 4.22 mol), p-toluenesulfonic acid monohydrate (6.7 g, 35.2 mmol) and toluene (2.0 L, 10 V) were placed in a 3 L single mouth bottle, installed with a water separator and a condenser tube, stirred and heated to reflux reaction for 2 h.

After cooled, the reaction solution was poured into water (800 mL, 4 V), and subjected to a separatory funnel. The aqueous phase was extracted with ethyl acetate:tetrahydrofuran=5:1 (200 mL, 1 V), and the organic phases were combined. The organic phase was washed with water (300 mL, 1.5 V) and saturated brine (300 mL, 1.5 V), and dried over anhydrous sodium sulfate. After drying, the organic phase was filtered out, and the solvent was removed by rotary evaporation to obtain a crude product. The crude product was dissolved in ethyl acetate (1.0 L, 5 V) under heat, followed by the addition of n-heptane (400 mL, 2 V) and cooled to room temperature, stirred and crystallized for 1 h. The filter cake was washed with ethyl acetate:n-heptane=2.5:1 (150 mL, 0.75 V), drained, and vacuum dried under 20-30° C. to obtain compound 1.3 (196.2 g, yield: 85.0%).

$^1$H-NMR (400 MHz, $CDCl_3$) δ:5.75 (s, 1H), 5.54 (d, J=5.8 Hz, 1H), 3.93 (m, 2H), 3.88 (m, 2H), 2.64-2.30 (m, 6H), 2.26-1.97 (m, 7H), 1.87 (m, 1H), 1.73-1.65 (m, 1H), 1.35 (s, 3H), 1.11 (m, 1H), 0.86 (s, 3H).

Example 3: Synthesis of Compound 1.4

Compound 1.3 (150.0 g, 456.8 mmol), Pd/C (15.0 g, 10%), N-methylpyrrolidone (1.5 L, 10 V) were placed in a pressurized reactor with hydrogen replacement, and stirred for 6 h under room temperature and the condition of 40-60 psi, 150 rpm.

Ethyl acetate (750 mL, 5 V) was added, and Pd/C was removed by filtration. Water (750 mL, 5V) was added, the aqueous phase was extracted twice with ethyl acetate (300 mL, 2 V), and the organic phases were combined. The organic phase was washed with water (450 mL, 3 V) and saturated brine (450 mL, 3 V), dried over anhydrous sodium sulfate, and filtered to obtain an organic phase. Remove solvent by rotary evaporation to obtain compound 1.4 (135.8 g, yield 90.0%).

After TLC and ELSD examination, the compound 1.4 was entirely in 5β configuration, and no structure of 5α configuration was found.

$^1$H-NMR (400 MHz, $CDCl_3$) δ:5.44 (d, J=5.6 Hz, 1H), 3.94-3.92 (m, 4H), 2.50-2.40 (m, 2H), 2.17 (m, 2H), 2.14-1.95 (m, 7H), 1.86-1.69 (m, 4H), 1.49 (m, 4H), 1.10 (s, 3H), 0.99-0.87 (m, 1H), 0.81 (s, 3H).

Example 4: Synthesis of Compound 1.5

Compound 1.4 (130.0 g, 393.4 mmol) and tetrahydrofuran (1.3 L, 10 V) were put into a 2 L three-necked flask, and was stirred to dissolve under nitrogen protection. Cool to −5 to 5° C., add LiAl (OtBu) 3H (786.8 mL, 786.8 mmol, 1.0 M) dropwise, and stir under room temperature for 30 min. 7% p-toluenesulfonic acid (260 mL, 2 V) was dropwise added, and stirred under room temperature for 6 h. Add water (520 mL, 4V), extract using ethyl acetate (520 mL, 4 V), and the organic phases were combined. The organic phase was washed with water (520 mL, 4 V) and saturated brine (390 mL, 3 V), dried over anhydrous sodium sulfate, and filtered to obtain an organic phase. Remove solvent by rotary evaporation to obtain a crude product. The crude product was beated and washed for 1 h with acetone:n-heptane=1:8 (390 mL, 3 V) under room temperature, and drained under 20° C. to obtain compound 1.5 (107.8 g, yield: 95.0%).

$^1$H-NMR (400 MHz, CDCl$_3$) δ:5.42 (d, J=5.6 Hz, 1H), 3.73-3.60 (m, 1H), 2.46 (m, 1H), 2.23-1.98 (m, 7H), 1.80-1.70 (m, 2H), 1.57-1.36 (m, 7H), 1.33-1.13 (m, 3H), 1.09 (s, 3H), 0.82 (s, 3H).

Example 5: Synthesis of Compound 1.6

Compound 1.5 (30.0 g, 104 mmol), DMAP (1.22 g, 10 mmol) and triethylamine (30.4 g, 300 mmol) were dissolved in 300 mL of dichloromethane. Benzoyl chloride (28.1 g, 200 mmol) was dropwise added thereto under room temperature. Upon completion of the dropwise adding, raise the temperature until reflux, and react for 10 hours. When TLC shows complete reaction, the reaction was stopped. The reaction solution was cooled to room temperature and 200 mL of dichloromethane was further added. The reaction solution was washed once with 100 mL of water, and the organic phase was washed once with 2N HCl (150 mL) and once with saturated brine (100 mL). The solvent was removed under reduced pressure to obtain an oily matter, and the oily matter was dissolved in 300 mL of acetone. 50 mL of water was slowly added thereto, solids were gradually precipitated. Cool to 0-5° C. for 2-4 hours, and filtered to obtain white powder solid compound 1.6 (38.2 g, yield: 95%).

$^1$HNMR (400 MHz, CDCl$_3$) δ:8.05 (dd, J=8.2, 1.0 Hz, 2H), 7.55 (m, 1H), 7.45 (m, 2H), 5.49 (d, J=5.6 Hz, 1H), 5.08-4.93 (m, 2H), 2.49 (m, 1H), 2.32-1.99 (m, 7H), 1.95-1.85 (m, 1H), 1.84-1.51 (m, 7H), 1.48-1.20 (m, 3H), 1.15 (s, 3H), 0.85 (s, 3H).

Example 6: Synthesis of Compound 1

Under nitrogen protection, triphenyl ethyl phosphonium bromide (41.6 g, 112 mmol) was dissolved in 150 mL of tetrahydrofuran. Potassium tert-butoxide (12.6 g, 112 mmol) was added to the mixture suspension under 20-30° C. (the reaction solution turned orange), and stirred under room temperature for 1 hour. 100 ml of a tetrahydrofuran solution dissolved with compound 1.6 (20 g, 51 mmol) was added dropwise in 20 minutes. React under room temperature for 2 hours. TLC showed complete conversion of the starting material. The reaction solution was poured into 400 mL of iced water. Methyl tert-butyl ether (50 mL)×2 was added for liquid separation and extraction. The organic layer was washed by saturated brine (40 mL). Solvent was removed under reduced pressure, leaving about 40 mL of volume. 200 mL of isopropyl alcohol was added. Tetrahydrofuran was removed under reduced pressure. While 100 mL of solvent was left, a large amount of solids were already precipitated, and 20 mL of water was dropwise added thereto. The crystallization solution was cooled to 0-5° C., stirred and crystallized for 1 hour, and filtered to obtain white needle-shaped crystals. Compound 1 (17.5 g, yield: 85%) was dried under 40-50° C. by a blower.

$^1$H-NMR (400 MHz, CDCl$_3$) δ:8.06 (m, 2H), 7.55 (t, J=8.0, 8.0 Hz, 1H), 7.44 (t, J=8.0, 8.0 Hz, 2H), 5.46 (s, 1H), 5.22 (m, 1H), 5.03 (m, 1H), 2.48-2.37 (m, 3H), 2.33-2.20 (m, 1H), 2.20-2.00 (m, 3H), 1.94-1.84 (m, 1H), 1.81-1.60 (m, 9H), 1.51-1.16 (m, 5H), 1.13 (s, 3H), 0.84 (s, 3H).

Example 7: Synthesis of Compound 2

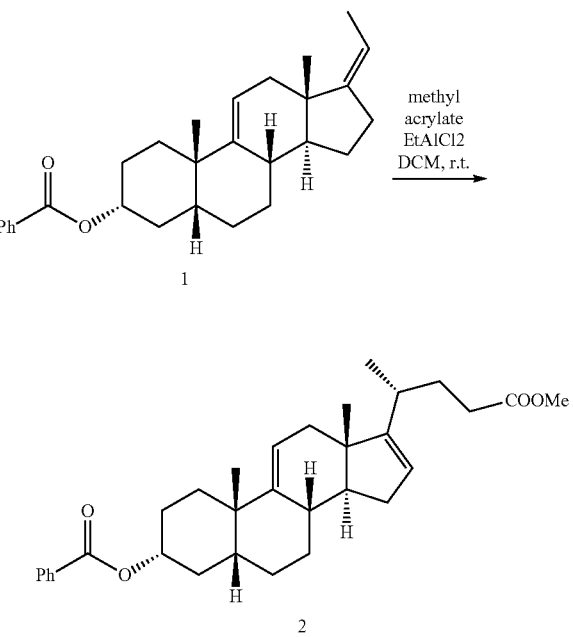

Compound 1 (220 g, 544 mmol) and dichloromethane (2200 mL, 10 V) were added to a 5,000 mL three-necked round bottom flask, stirred to dissolve, and subjected to nitrogen replacement. The reaction system was cooled to between −5 to 5° C. Methyl acrylate (117 g, 1360 mmol) was added dropwise in about 15 min, and proceeded with stirring for 30 minutes. The temperature of the reaction system was controlled under −5-5° C. Subsequently, a solution of diethylaluminium chloride (25% hexane solution, 829 mL, 1631 mmol) was added dropwise, and after continuously stirring for 30 min, raise the temperature of the reaction system to 25 to 30° C., and stirred for reaction for 48 hours. As monitored by HPLC (area normalization method), when compound 1<3%, the reaction was stopped.

Under stirring condition, the reaction solution was slowly added to ice-water mixture (4,400 g, 20 V), subjected to liquid separation and extraction, and the organic phases were combined. The organic phase was washed successively with 1 mol/L of hydrochloric acid (2,200 ml, 10 V) and 10% of sodium chloride solution (2,200 mL, 10 V). After removal of the solvent of the organic phase under reduced pressure, isopropanol (1320 ml, 6V) was added and the distillation was continued under reduced pressure until the density of the distilled liquid was consistent with that of the isopropanol. Isopropyl alcohol (1,320 ml, 6V) was further added, and then water (275 ml, 1.25V) was added dropwise. A large amount of solids were precipitated. Stir under 20 to 30° C. for 2 hours and then cool to 0 to 5° C., followed by stirring for 2 hours. Stop stirring and filter. The filter cake was washed with a small amount of low-temperature isopropanol/water (4/1), drained, and dried at 50° C. by a blower until the moisture was less than 1% to obtain compound 2 (238 g, yield: 89%).

$^1$H-NMR (400M, DMSO-d6) δ:7.93-7.95 (d, 2H), 7.63-7.67 (t, 1H), 7.49-7.53 (t, 3H), 5.43 (s, 1H), 5.34 (s, 1H), 4.92 (s, 1H), 3.58 (s, 3H), 2.21-2.26 (m, 2H), 2.10-2.14 (m, 4H), 1.95-2.03 (m, 2H), 1.81-1.87 (m, 2H), 1.71-1.72 (m, 1H), 1.54-1.70 (m, 5H), 1.47-1.53 (q, 1H), 1.33-1.35 (d, 2H), 1.16-1.19 (q, 1H), 1.10 (s, 3H), 1.02-1.03 (d, 1H), 1.01-1.02 (d, 3H), 0.65 (s, 3H).

m.p.=109-109.7° C.

$[\alpha]_D^{20}$=+68.8 (c=1, chloroform).

HPLC (UV, aera): 98.4%.

Example 8: Synthesis of Compound 3

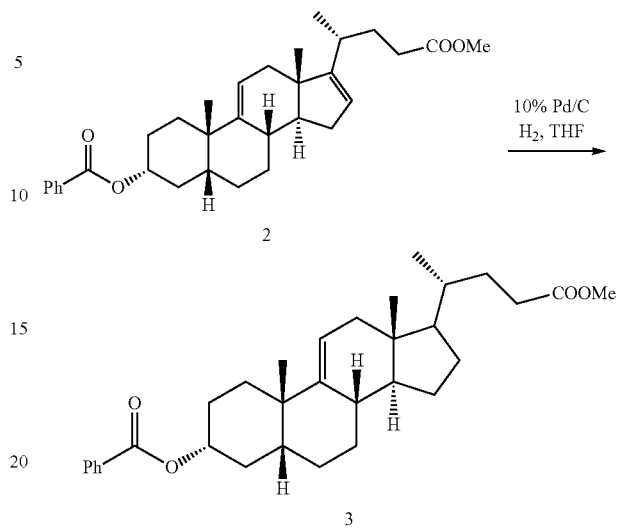

After compound 2 (1,000 g, 2.04 mol), tetrahydrofuran (5000 mL, 5V), and 10% Pd/C (50% wt, 120 g, 12% wt) were added to a 1.0 L clean autoclave, the device was sealed, and subjected to nitrogen replacement and then hydrogen replacement. React for 24 hours with the hydrogen pressure maintained 1.2 MPa. As monitored by HPLC (area normalization method), when compound 2<2%, the reaction was stopped. After nitrogen replacement, the reaction slurry was taken out and filtered. Solvent was removed from the filtrate under reduced pressure. After addition of acetonitrile (2,000 mL, 2 V), proceed with distillation under reduced pressure to remove solvent, followed by addition of acetonitrile (12 L, 12 V) and heated to clearly dissolve. The next reaction was carried out directly without purification.

Example 9: Synthesis of Compound 4

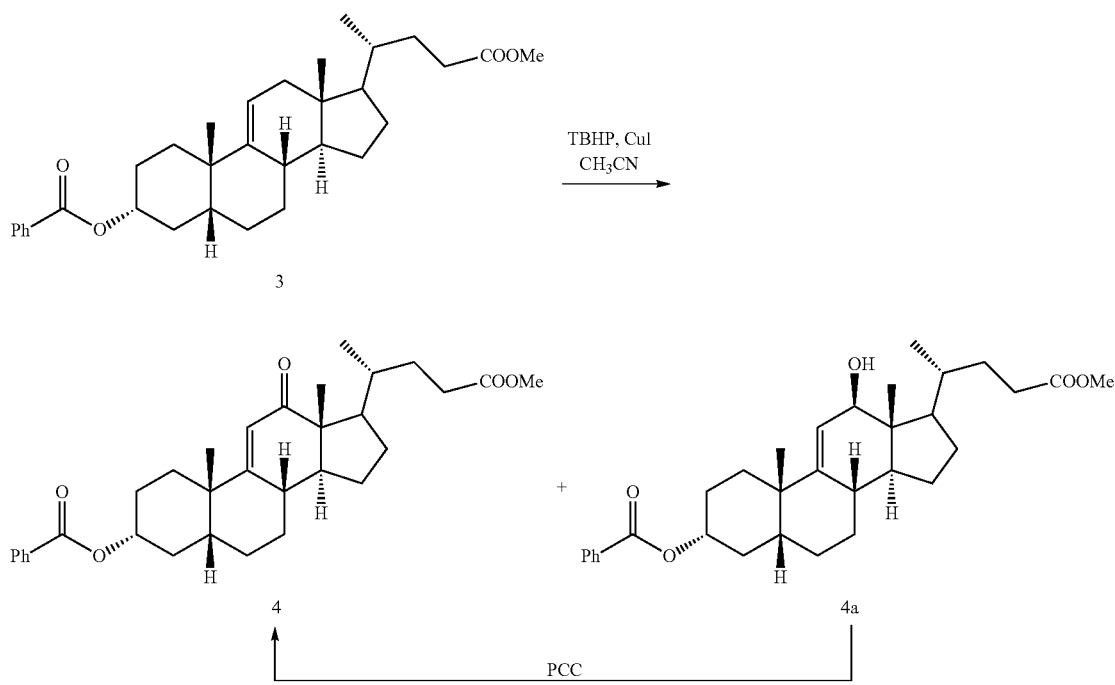

The temperature of the reaction solution of compound 3 and acetonitrile obtained in Example 8 was controlled under 45 to 50° C. After copper iodide (309 g, 1624 mmol) was added thereto, add TBHP (70%) (783 g, 6089 mmol) and proceed with stirring for 24 hours. As monitored by HPLC (area normalization method), when compound 3<2%, the reaction was stopped. The temperature of the reaction system was lowered to 15 to 25° C., followed by addition of ethyl acetate (5.0 L, 5V). Saturated solution of sodium sulfite (5.0 L, 5V) was added dropwise, stirred, and filtered. Saturated sodium chloride solution (3.0 L, 3 V) was added to the filtrate, stirred, and subjected to liquid separation. The organic phases were combined and the solvent was removed under reduced pressure to keep the volume of the system at about 13 L.

The system temperature of the above-mentioned organic phase with solvent removed at 20 to 30° C. Pyridinium chlorochromate (481 g, 2233 mmol) was added in batches. As monitored by HPLC (area normalization method), when compound 4a<2%, the reaction was stopped. Ethyl acetate (5.0 L, 5V) was added and the insoluble was removed by filtration. Saturated sodium sulfite solution (5.0 L, 5V) and saturated sodium chloride solution (3.0 L, 3 V) was added to the filtrate, stirred, subjected to liquid separation, and the organic phases were combined. The organic phase was washed once with sodium chloride solution (3.0 L, 3 V), and the solvent of the organic phase was removed under reduced pressure. The organic phase was added to methylene chloride (3000 ml, 3V) and dissolved, and passed through silica gel column (100-200 mesh, 10.0 kg, 10 w.t.). Dichloromethane was used as eluent to collect the products. Part of dichloromethane solvent was removed under reduced pressure. n-heptane (15.0 L, 15 v) was added and maintained under reduced pressure to remove dichloromethane. A large amount of solids were precipitated from the system, and subjected to filtration to obtain compound 4 (713 g, yield: 71%).

$^1$H-NMR (400M, DMSO-d6) δ:7.93-7.95 (d, 2H), 7.62-7.64 (t, 1H), 7.48-7.52 (t, 3H), 5.64 (s, 1H), 4.93 (s, 1H), 3.58 (s, 3H), 2.41-2.49 (m, 1H), 2.34-2.36 (m, 1H), 2.22-2.26 (m, 1H), 2.10-2.13 (m, 2H), 1.86-1.88 (m, 2H), 1.64-1.75 (m, 6H), 1.32-1.55 (m, 7H), 1.20 (s, 3H), 1.24-1.26 (m, 2H), 0.91-0.93 (d, 3H), 0.86 (s, 3H).

m.p.=124.6-126.4° C.

$[α]_D^{20}$=+124.8 (c=1, chloroform).

HPLC (UV, aera): 96.9%.

Example 10: Synthesis of Compound 5

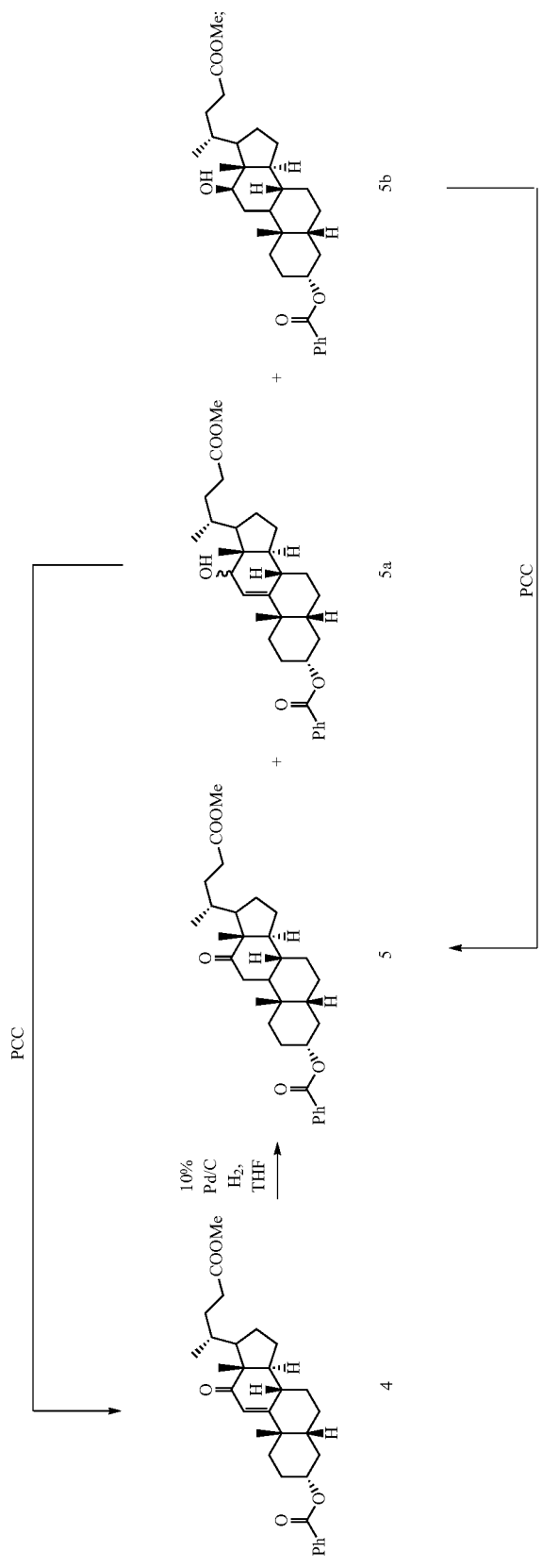

Compound 4 (600 g, 1184 mmol), tetrahydrofuran solution (6.0 L, 10 V), and 10% Pd/C (dry, 150 g, 25% w.t.) were added to a 10 L clean and dry autoclave, followed by nitrogen replacement and hydrogen replacement. The system pressure was kept at 1.2 Mpa. The reaction system was heated to 55-65° C. and stirred for 24 hours. As monitored by HPLC (area normalization method), when compound 5 account for 67%, alkene compound (5a) and the hydroxy compound (5b) account for 31%, and unknown impurities account for 2%, the reaction was stopped.

Pd/C was recovered by filtration. Solvent of the filtrate was removed under reduced pressure and dissolved in ethyl acetate (6.0 L, 10 V). The system temperature was controlled at 20-30° C. Pyridinium chlorochromate (76.4 g, 355 mmol) was added in batches, and proceeded with stirring for 12 hours. HPLC showed that enol compounds and hydroxyl compounds were less than 1%. Filter through a celite bed, wash the filtrate with water, and the organic phases were combined. The solvent of the organic phase was removed under reduced pressure and dissolved in tetrahydrofuran (6.0 L, 10V) to obtain a solution.

The solution was added to a 10 L clean and dry autoclave. The previously recovered Pd/C was added. The reaction was carried out for 24 hours under a temperature of 55 to 65° C. with a hydrogen pressure maintained at 1.5 MPa. As monitored by HPLC, compound 4 was <1%, and compound 5 accounted for 92%.

The reaction system was filtered with a 0.22 micron organic filter to remove Pd/C. Activated carbon (60 g, 10% w.t) was added and heated under reflux for 30 minutes. The reaction system was filtered with a 0.22 micron organic filter to remove activated carbon. The solvent of the filtrate was removed under reduced pressure, and dichloromethane (1800 ml, 3V) and methanol (4800 ml, 8V) were added. Dichloromethane was removed under reduced pressure, and white solids were precipitated during the procedure. Cool for crystallization. The system temperature was maintained at −5 to 0° C. and stirred for 2 hours. Stop stirring and perform filtration.

The filter cake was washed with cold methanol (600 mL, 1 V), drained, and forcedly air dried at 50° C. until constant weight to obtain compound 5 (510 g, yield: 85%).

$^1$H-NMR (400M, DMSO-d6) δ:7.95-7.96 (d, 2H), 7.62-7.66 (m, 1H), 7.49-7.52 (t, 2H), 4.84-4.89 (m, 1H), 3.57 (s, 3H), 2.44-2.54 (m, 1H), 2.30-2.37 (m, 1H), 2.17-2.25 (m, 1H), 1.58-1.92 (m, 13H), 1.22-1.49 (m, 8H), 1.05-1.17 (m, 2H), 1.02 (s, 3H), 0.97 (s, 3H), 0.75-0.77 (m, 3H).

m.p.=123.2-125.2° C.

$[\alpha]_D^{20}$=+107.3 (c=1, chloroform).

HPLC (UV, aera): 97.2%.

Example 11: Synthesis of Compound 6

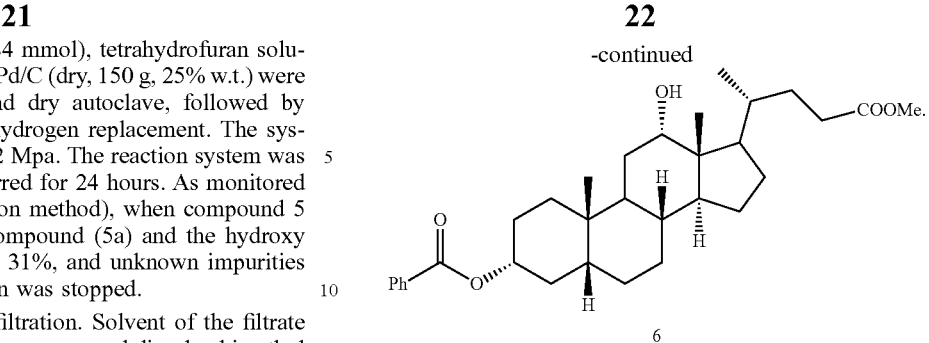

Compound 5 (170 g, 334 mmol) and tetrahydrofuran (1020 ml, 6 V) were added to a 3,000 ml three-necked round bottom flask under nitrogen protection and stirred for dissolving. The system temperature was controlled at −5 to 5° C. A solution of lithium tri-t-butoxyaluminium hydride tetrahydrofuran (501 mL, 501 mmol) was dropwise added. After completing the dropwise addition, proceed with stirring for 24 hours at −5 to 5° C. As monitored by HPLC (aera), when compound 5<1%, the reaction was stopped. The system was cooled, and the system temperature was maintained at not higher than 10° C. 2 mol/L hydrochloric acid (600 ml) was added dropwise, subjected to liquid separation, and the organic phases were combined. Stir and wash with saturated sodium chloride (170 ml, 1 V) and 2 mol/L hydrochloric acid (170 ml, 1 V) together, and perform liquid separation to obtain an organic phase. Wash with saturated sodium chloride (340 ml, 2 V), and perform liquid separation to obtain an organic phase. Part of the solvent of the organic phase was removed under reduced pressure. When the left solvent volume was about 300 ml, N-heptane (1700 ml, 10V) was added, stirred, and subjected to liquid separation to obtain an organic phase. After tetrahydrofuran was removed by distillation under reduced pressure (determined by the consistency between the densities of the distilled liquid and n-heptane), and at the same time the volume of the system was assured to be about 1,700 ml of solution, stir for 2 hours at 10 to 25° C. and perform filtration. The filter cake was washed with a small amount of n-heptane and drained to obtain compound 6 (145 g, yield: 85%).

$^1$H-NMR (400M, DMSO-d6) δ:7.96-7.98 (d, 2H), 7.63-7.67 (t, 1H), 7.50-7.54 (t, 2H), 4.88 (m, 1H), 4.27-4.28 (m, 1H), 4.27-4.28 (d, 1H), 3.80-3.81 (d, 1H), 3.60 (s, 3H), 2.28-2.35 (m, 1H), 2.16-2.24 (m, 1H), 1.85-1.97 (m, 2H), 1.68-1.82 (m, 6H), 1.55-1.66 (m, 4H), 1.48-1.51 (m, 2H), 1.32-1.48 (m, 4H), 1.14-1.28 (m, 3H), 0.96-1.14 (m, 3H), 0.93 (s, 3H), 0.91 (s, 3H), 0.61 (s, 3H).

m.p.=107.7-112.3° C.

$[\alpha]_D^{20}$=+50.9 (c=1, chloroform).

HPLC (UV, aera): 98.81%.

Example 12: Synthesis of Crude Deoxycholic Acid

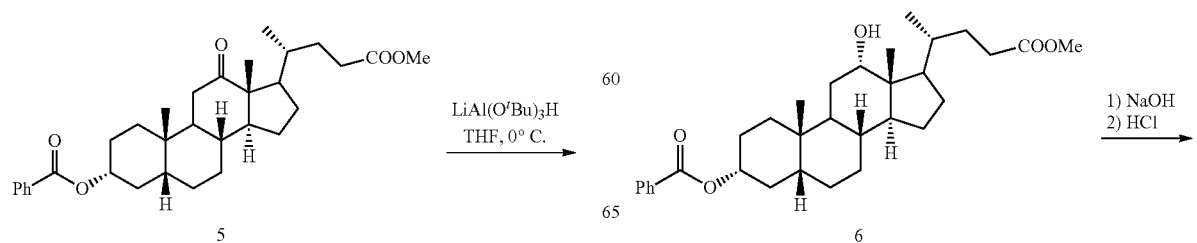

-continued

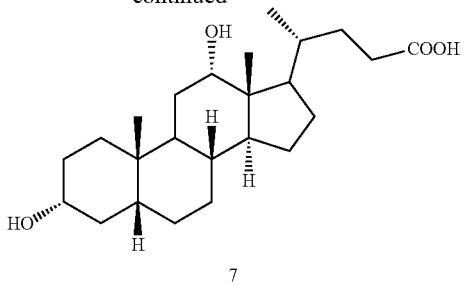

7

Compound 6 (100 g, 196 mmol), tetrahydrofuran (600 g, 6 V) and methanol (600 mL, 6 V) were added to a 2,000 ml three-necked round bottom flask, and stirred for dissolving. The system temperature was maintained below 25° C. 4 mol/L sodium hydroxide solution (196 ml, 784 mmol) was added dropwise and stirred for 24 hours at a temperature of 20-30° C. The completion of reaction was monitored by HPLC. After water (800 ml, 8V) was added to decrease the system temperature to 10-15° C., 1 mol/L hydrochloric acid was added dropwise to adjust pH to 9-10. Organic solvent was then removed under reduced pressure, cooled to 10-25° C., and washed twice with dichloromethane (500 ml*2). The pH was adjusted to 1 to 2 with 1 mol/L hydrochloric acid, stirred for 2 hours and filtered. The filtrate was washed with water (500 ml, 5 V), drained, and forcedly air dried to obtain 101 g of solid. Under 15-25° C., the product was dissolved in methyl tert-butyl ether (1,000 ml, 10 V), stirred for 12 hours or more, and filtered. After the filter cake was washed with methyl tert-butyl ether (400 ml, 4V), it was forcedly air dried to obtain a crude product of deoxycholic acid (73.1 g, 95%).

Example 13: Purification of Deoxycholic Acid

Crude deoxycholic acid (100 g, 196 mmol) and dichloromethane solution (1500 ml, 15 V) with 10% methanol were added to a 2,000 ml three-necked round bottom flask, and heated and stirred for dissolving. The insoluble was removed by filtration, and proceeded with distillation by heating, with dropwise addition of dichloromethane (2000 ml) at the same time, ensuring the consistency between the rates of dropwise addition and of liquid distillation. The methanol content passing through the gas phase measurement system was between 2.5% and 3%. The temperature was lowered to 5-10° C., stirred for 2 hours and then filtered. The filter cake was washed with dichloromethane (200 ml, 2 V), and forcedly air dried. The maximum single impurity as determined by HPLC (ELSD) was below 0.1%. The resulting product (dichloromethane) was added to water (1,000 ml), and a sodium hydroxide solution was added to adjust pH to 9-10. Then 1 mol/L hydrochloric acid was added to adjust pH to 1-2. After stirring for 2 hours at 10 to 25° C., perform filtration and the filter cake was washed with water (500 ml). The filter cake was then pulped with pure water (2,000 ml, 20 V) for 4-8 h at 60-80° C., and then filtered and drained. After drying, pure product of deoxycholic acid was obtained (92 g, yield: 92%).

$^1$H-NMR (400M, DMSO-d6) δ:11.99 (s, 1H), 4.38-4.58 (m, 1H), 4.21-4.30 (m, 1H), 3.71-3.79 (m, 1H), 3.30-3.51 (m, 2H), 2.12-2.31 (m, 1H), 2.05-2.12 (m, 1H), 1.71-1.91 (m, 4H), 1.42-1.71 (m, 5H), 1.28-1.38 (m, 9H), 1.15-1.25 (m, 3H), 1.11 (s, 3H), 0.95-1.08 (m, 2H), 0.91 (d, 3H), 0.86 (s, 3H).

m.p.=173.2-174.1° C.

$[\alpha]_D^{20}$=+68.8 (c=1, chloroform); $[\alpha]_D^{20}$=+55.4 (c=1, ethanol).

HPLC (ELSD) purity: 99.9%.

What is claimed is:

1. A method for preparing (DCA) or an ester thereof or a pharmaceutically acceptable salt thereof:

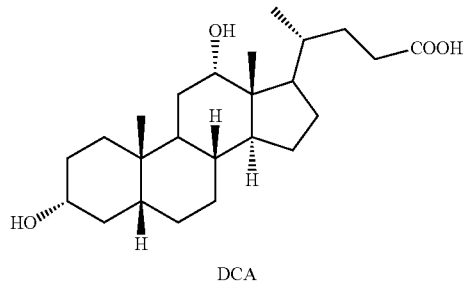

DCA said method comprising, c) reacting a compound of formula 1.3 with $H_2$ under a hydrogenation condition to form a compound of formula 1.4

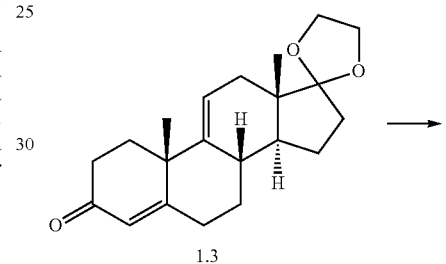

1.3

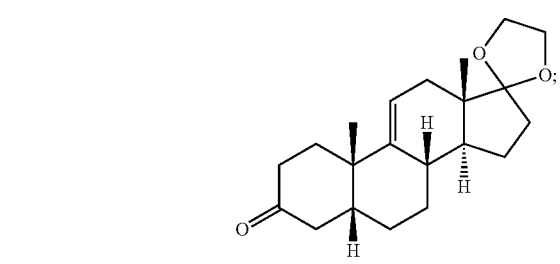

1.4 d) subjecting the compound of formula 1.4 to carbonyl reduction and deprotection to obtain a compound of formula 1.5

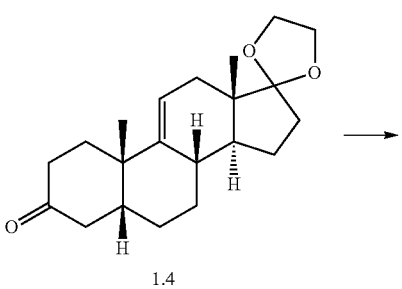

1.4

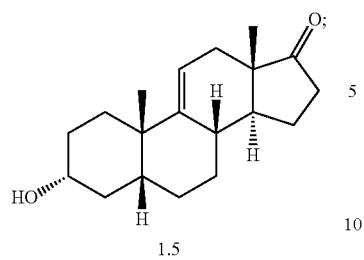

1.5 e) reacting the compound of formula 1.5 with benzoyl chloride to form a compound of formula 1.6

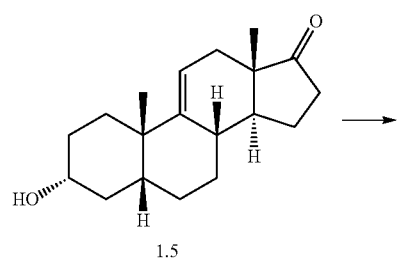

1.5

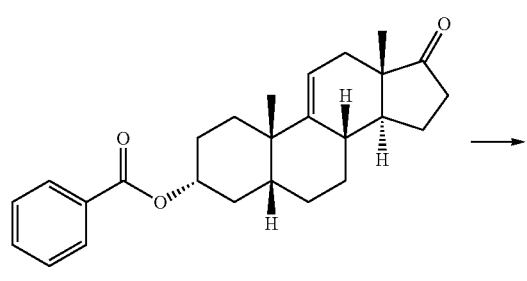

1.6 f) reacting the compound of formula 1.6 with a dicarbene transfer reagent under an olefin forming condition to form a compound of formula 1

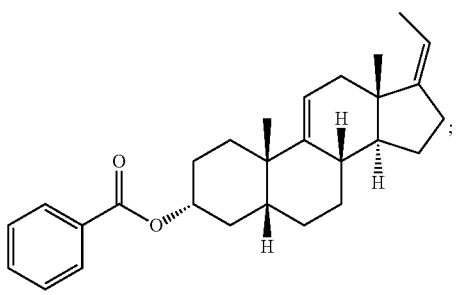

1 g) reacting the compound of formula 1 with methyl acrylate in the presence of a Lewis acid to form a compound of formula 2

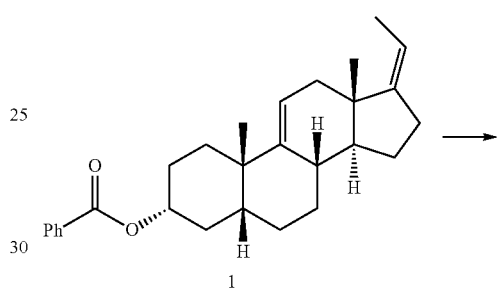

1

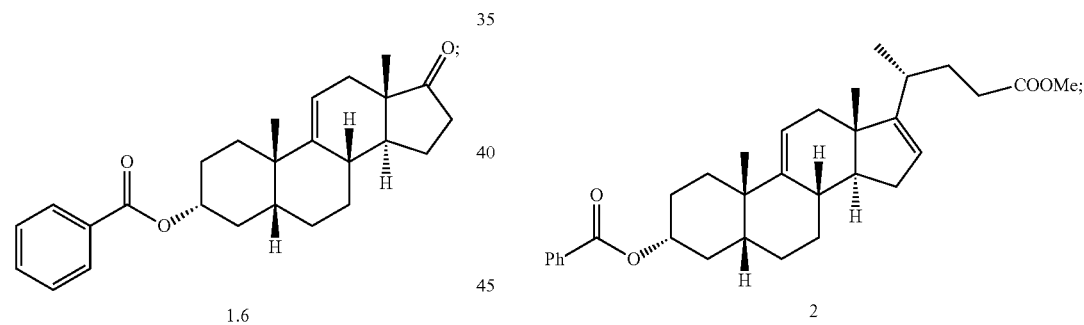

2 h) reacting the compound of formula 2 with $H_2$ under a hydrogenation condition to form a compound of formula 3

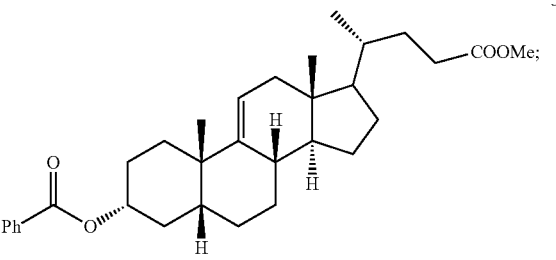

i) reacting the compound of formula 3 with an oxidizing agent to form a compound of formula 4

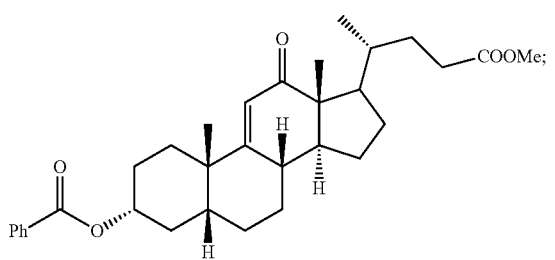

j) reacting the compound of formula 4 with H₂ under a hydrogenation condition to form a compound of formula 5

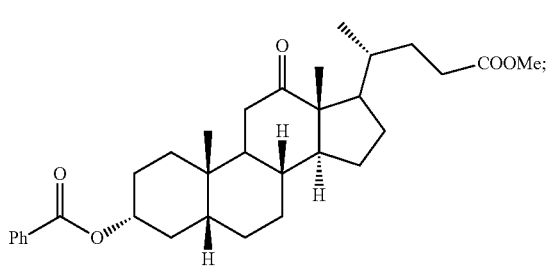

k) reacting the compound of formula 5 with a reducing agent to form a compound of formula 6

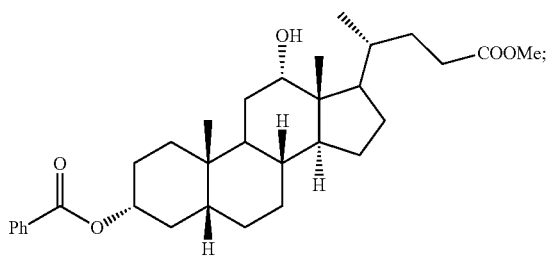

and l) exposing the compound of formula 6 to a deprotection condition to form an ester thereof, and optionally, exposing to a suitable hydrolysis condition to form a deoxycholic acid or a pharmaceutically acceptable salt thereof.

2. The method of claim 1, wherein the hydrogenation condition in c) is pd/C as a catalyst and N-Methylpyrrolidone as a solvent.

3. The method of claim 1, wherein the condition of the carbonyl reduction and deprotection in d) is dissolving the compound 1.4 in tetrahydrofuran, dropwise adding LiAl(OtBu)₃H at −5 to 5° C., stirring at room temperature, and followed by dropwise adding p-toluenesulfonic acid.

4. The method of claim 1, wherein the dicarbene transfer reagent in f) is Ph₃PCH₂CH₃Br, KOtBu; the Lewis acid in g) is EtAlCl₂; the hydrogenation condition in h) comprises pd/C or PtO₂ as a catalyst; the oxidation condition in i) comprises tert-butylhydroperoxide and pyridinium chlorochromate; the hydrogenation condition in j) comprises pd/C or PtO₂ as a catalyst; the reducing agent in k) is LiAl(OtBu)₃H.

5. The method of claim 1, wherein the deprotection and the hydrolysis condition in 1) comprise reacting the compound 6 with an alkali metal hydroxide, an alkali metal alcoholate, an alkaline earth metal hydroxide, an alkaline earth metal alcoholate, or a mixture thereof.

6. The method of claim 5, wherein the alkali metal hydroxide is NaOH.

7. A method for preparing a compound of formula 1.4, said method is: reacting a compound of formula 1.3 with H₂ to form the compound of formula 1.4, with N-Methylpyrrolidone as a solvent and 10% pd/C as a catalyst

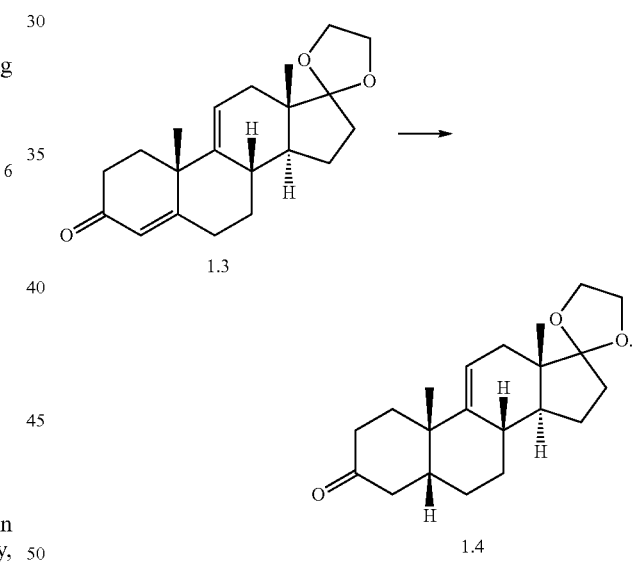

* * * * *